US011078297B2

(12) United States Patent
Reed

(10) Patent No.: US 11,078,297 B2
(45) Date of Patent: Aug. 3, 2021

(54) PROPHYLAXIS OF THROMBOSIS

(71) Applicant: Translational Sciences, Inc., Memphis, TN (US)

(72) Inventor: Guy L. Reed, Memphis, TN (US)

(73) Assignee: Translational Sciences, Inc., Memphis, TN (US)

( * ) Notice: Subject to any disclaimer, the term of this patent is extended or adjusted under 35 U.S.C. 154(b) by 473 days.

(21) Appl. No.: 15/536,948

(22) PCT Filed: Dec. 21, 2015

(86) PCT No.: PCT/US2015/067028
§ 371 (c)(1),
(2) Date: Jun. 16, 2017

(87) PCT Pub. No.: WO2016/106186
PCT Pub. Date: Jun. 30, 2016

(65) Prior Publication Data
US 2018/0355058 A1 Dec. 13, 2018

Related U.S. Application Data

(60) Provisional application No. 62/095,462, filed on Dec. 22, 2014.

(51) Int. Cl.
*A61K 39/395* (2006.01)
*C07K 16/38* (2006.01)
*A61P 9/10* (2006.01)
*A61K 39/00* (2006.01)
*A61K 38/17* (2006.01)

(52) U.S. Cl.
CPC ............... *C07K 16/38* (2013.01); *A61P 9/10* (2018.01); *A61K 38/1774* (2013.01); *A61K 2039/505* (2013.01)

(58) Field of Classification Search
None
See application file for complete search history.

(56) References Cited

U.S. PATENT DOCUMENTS

| 5,534,255 | A | * | 7/1996 | Sumi | C07K 14/8121 424/141.1 |
| 5,582,862 | A | * | 12/1996 | Reed | A61K 38/49 424/141.1 |
| 6,114,506 | A | | 9/2000 | Reed et al. | |
| 7,309,774 | B2 | | 12/2007 | McKee et al. | |
| 9,150,903 | B2 | * | 10/2015 | Reed | C12Q 1/56 |
| 9,834,614 | B2 | * | 12/2017 | Reed | C12Q 1/56 |
| 2002/0086025 | A1 | | 7/2002 | Reed | |
| 2003/0017147 | A1 | | 1/2003 | Reed | |
| 2003/0031664 | A1 | | 2/2003 | Reed | |
| 2010/0086536 | A1 | | 4/2010 | Reed | |
| 2014/0220034 | A1 | | 8/2014 | Reed | |

FOREIGN PATENT DOCUMENTS

| EP | 0272609 A2 | 6/1988 | | |
| WO | 99/61072 A2 | 12/1999 | | |
| WO | 2004/042000 A2 | 5/2004 | | |
| WO | 2006/005583 A2 | 1/2006 | | |
| WO | WO-2008134577 A1 | * | 11/2008 | ............... C12Q 1/56 |
| WO | WO-2013036596 A2 | * | 3/2013 | ............. C07K 16/18 |

OTHER PUBLICATIONS

Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Abdul et al., PLoS One May 3, 2018;13(5):e0196911. doi: 10.1371/journal.pone.0196911. eCollection 2018.*
Mimuro et al., Blood Feb. 1987;69(2):446-53.*
PCT International Search Report and Written Opinion for PCT Application No. PCT/US2015/067028 dated Mar. 3, 2016 (6 pages).
Reed et al., "Inhibition of Clot-Bound Alpha2-Antiplasmin Enhances in Vivo Thrombolysis," Circulation, 1990, 82(1):164-168.
Mimuro et al., "Monoclonal Antibodies to Discrete Regions in Alpha2-Plasmin Inhibitor," Blood, 1987, 69(2):446-453.
Anonick et al., "Soluble Fibrin Preparations Inhibit the Reaction of Plasmin with Alpha-2-Macroglobulin: Comparison with Alpha-2-Antiplasmin and Leupeptin," Biochem. J., 1991, vol. 275, pp. 53-59.
Holmes et al., "Characterization of Recombinant Human α2-Antiplasmin and of Mutants Obtained by Site-Directed Mutagenesis of the Reactive Site," Biochemistry, 1987, vol. 26, p. 5133.
Potempa et al., "Alpha-2-Antiplasmin: A Serpin with Two Separate but Overlapping Reactive Sites," Science, 1988, vol. 241, No. 4866, pp. 699-700 (abstract only).
International Search Report for PCT/US08/061662 dated Aug. 18, 2008 (1 page).
Sazonova et al., "Fibrinolysis is Amplified by Converting alpha 2-Antiplasmin from a Plasmin Inhibitor to a Substrate," Journal of Thrombosis and Haemostasis, 2007, 5:2087-2904.

* cited by examiner

*Primary Examiner* — Michael Szperka
(74) *Attorney, Agent, or Firm* — Eversheds Sutherland (US) LLP

(57) ABSTRACT

The invention provides a method and composition for preventing thrombosis and complications associated therewith by targeting Sf2 directly. The invention provides Sf2-deficiency or prophylactic administration of a therapeutic agent, such as a Sf2 antagonist or a Sf2 antibody, markedly reduces thrombus formation that would otherwise be caused due to surgery, immobility, genetic abnormality, cancer, trauma, or other risk factors.

10 Claims, 2 Drawing Sheets

PROPHYLAXIS OF THROMBOSIS

CROSS-REFERENCE TO RELATED APPLICATIONS

This application claims the priority benefit of PCT/US2015/067028 filed on Dec. 21, 2015 which claims priority benefit of U.S. Provisional Patent Application Ser. No. 62/095,462, filed Dec. 22, 2014, the entire contents of which are hereby incorporated by reference herein.

FIELD OF THE INVENTION

The invention relates to methods of preventing the formation of thrombosis and its associated complications.

BACKGROUND OF THE INVENTION

Venous thromboembolism (VTE) is a common problem that affects about 133 people per year per 100,000 population and recent estimates suggest that the incidence of VTE may be rising.[1] Annual direct costs for medical management are up to $10 billion;[2, 3] the additional costs of chronic disability due to complications resulting from VTE (pulmonary hypertension, leg pain, swelling, ulcers, etc.) are unknown. In patients with VTE, the mortality rate is 10-30%, primarily due to pulmonary embolism.[3] VTE leads to chronic complications such as post-thrombotic syndrome in as many as 50% of patients, despite standard of care therapy. Venous thrombosis is a particular problem in hospitalized patients, particularly in those undergoing major surgeries.[4] In these patients, where there is a significant risk of bleeding, it is crucial to identify better methods of prophylaxis against the development of VTE.

The only effective agents for preventing venous thrombosis target the coagulation pathway which triggers the formation of cross-linked fibrin and the activation of platelets; these are the critical components of a thrombus.[5] Established therapies such as warfarin interfere with vitamin K-dependent coagulation factors such factors II, VII, IX and X.[5] Unfractionated heparin modifies the function of antithrombin to inactivate thrombin, while low molecular weight heparin acts on antithrombin to increase inhibition of factor Xa.[5] Several newer oral anticoagulant drugs are direct inhibitors of thrombin or of factor Xa. However, all current strategies for prophylaxis of venous thromboembolism carry a significant risk of hemorrhage.[5]

There is a need for effective prophylaxis of thrombus formation that is not associated with significant bleeding risk. Serpin f2 (also known as Sf2, plasmin inhibitor, and alpha2-antiplasmin) is a serine protease inhibitor of coagulation factor Xia, activated protein C, and plasmin[6, 7] Recent studies have shown that Sf2 inhibition and Sf2 deficiency are tolerated without significant bleeding risk. Still, the functional significance of these interactions is unknown and the contribution of Sf2 to thrombus formation has been unclear.

SUMMARY OF THE INVENTION

The invention provides a method for preventing thrombus formation or complications associated therewith by targeting Sf2 directly. More specifically, the invention provides that Sf2 affects thrombus formation via modulation of factor XIa and activation of protein C, and Sf2 deficiency or inactivation can be used as a safe prophylaxis against the development of venous thromboembolism.

In certain embodiments, the invention provides a method and composition for preventing thrombus formation or complications associated therewith in a patient at risk comprising administering a prophylactic amount of a therapeutic agent targeting Sf2 directly. in certain embodiments, the therapeutic agent used in the invention method and/or composition is a Sf2 antagonist that directly interferes with or inhibits Sf2 causing Sf2-deficiency. In other embodiments, the therapeutic agent used in the invention method and/or composition is a Sf2 antibody, or a functional fragment thereof, including but not limited to, a monoclonal or polyclonal antibody, a recombinant or naturally occurring antibody, a human or humanized antibody. Exemplary Sf2 antibody used in the invention includes, but is not limited to, Sf2 antibody 4h9 (innov-research.com/product/inhibitory-mouse-monclonal-to-mouse-antiplasmin-map4h9/), Sf2 antibody 27c9 (innov-research.com/product/inhibitory-mouse-monclonal-to-mouse-antiplasmin-map27c9/), and TS23 (Translational Sciences). The invention encompasses any Sf2 antagonist and/or Sf2antibody, now known or later developed, that interferes with or inhibits Sf2 directly, Methods for identifying and/or screening for such therapeutic agents are known in the art and are contemplated in the scope of the invention.

In certain embodiments, the invention method and/or composition is used for preventing thrombus formation or complications associated therewith due to surgery, immobility, genetic abnormality, cancer, trauma, or other risk factors. In certain embodiments, the inventive composition further comprises any physiologically acceptable carriers, solvent, or excipients, well-known now or later developed for use in a medicament.

In some aspects, the present disclosure relates to U.S. application Ser. No. 12/597,311, filed Oct. 23, 2009, which is now U.S. Pat. No. 9,150,903, International Application No. PCT/US2008/061662, filed Apr. 25, 2008 and published as WO 2010/0086536, and U.S. provisional patent application Ser. No. 60/913,913, filed Apr. 25, 2007. In some aspects, the present disclosure relates to U.S. application Ser. No. 08/933,983, filed Sep. 19, 1997, which is now U.S. Pat. No. 6,114,506, and U.S. provisional patent application Ser. No. 60/026,356, filed Sep. 20, 1996. In some aspects, the present disclosure relates to U.S. application Ser. No. 14/198,804, filed Mar. 6, 2014 and published as US 2014/0220034, International Application No. PCT/US2012/053900, filed Sep. 6, 2012 and published as WO 2013/036596, and U.S. provisional patent application Ser. No. 61/531,278, filed Sep. 6, 2011. The contents of the above applications are incorporated by reference in their entireties.

BRIEF DESCRIPTION OF THE DRAWINGS

FIG. 1A) Representative images of venous thrombi in IVCs isolated from sham, $Sf2^{+/+}$ and $Sf2^{-/-}$ mice. (Note the sham vena cava was ligated only at termination of experiment to facilitate removal). FIG. 1B) Thrombus weights normalized to mouse body weight (mg/g). Control ($Sf2^{+/+}$, N=7F, 4M), sham (N=4M), $Sf2^{-/-}$ (N=11F). Mean±SEM, ***p<0.001, ANOVA, Newman-Keuls correction.

DETAILED DESCRIPTION OF THE INVENTION

Figure 1A:
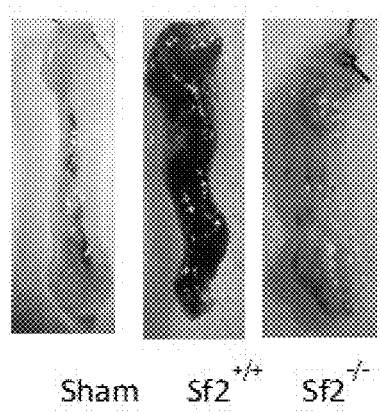
FIGS. 1A and 1B show that Sf2 deficiency prevents thrombus formation.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

It must be noted that as used herein and in the appended claims, the singular forms "a," "an," and "the," include plural forms unless the context clearly indicates otherwise. Thus, for example, reference to "an agent" includes one or more of such different agents, and reference to "the method" includes reference to equivalent steps and methods known to those of ordinary skill in the art that could be modified or substituted for the methods described herein.

The terms "comprising", "including" and "having" are intended to be inclusive and mean that there may be additional elements other than the listed elements.

As used herein, a "preventative" or "prophylactic" amount is meant to indicate an amount to effect elimination or postponement of development of a disease, a symptom of a disease, or medical condition, suppressing symptoms that may appear, or reducing the risk of developing or recurrence of a disease or symptom.

The term "pharmaceutically active" as used herein refers to the beneficial biological activity of a substance on living matter and, in particular, on cells and tissues of the body. A "pharmaceutically active agent" or "drug" is a substance that is pharmaceutically active and a "pharmaceutically active ingredient" (API) is the pharmaceutically active substance in a drug. As used herein, pharmaceutically active agents include synthetic or naturally occurring small molecule drugs and more complex biological molecules.

The term "pharmaceutically acceptable" as used herein means approved by a regulatory agency, listed in a generally recognized pharmacopoeia (e.g. U.S. Pharmacopoeia), or is otherwise safe for use in animals, and more particularly in humans and/or non-human mammals.

The term "pharmaceutically acceptable salt" as used herein refers to acid addition salts or base addition salts of compounds, such as a Sf2 antagonist, in the present disclosure. A pharmaceutically acceptable salt is any salt which retains the activity of the parent compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zürich, 2002; Berge et al., J Pharm. Sci. 66: 1, 1977). In some embodiments, a "pharmaceutically acceptable salt" is intended to mean a salt of a free acid or base of a compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

The term "pharmaceutically acceptable carrier" as used herein refers to an excipient, diluent, preservative, solubilizer, emulsifier, adjuvant, and/or vehicle with which a compound, such as a Sf2 antagonist, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

It is understood that aspects and embodiments of the invention described herein include "consisting" and/or "consisting essentially of" aspects and embodiments.

Unless otherwise defined, all technical and scientific terms used herein have the meaning as commonly understood by one of ordinary skill in the art to which this invention pertains. The practice of the present invention employs, unless otherwise indicated, conventional techniques of cell biology, molecular biology, genetics, chemistry, microbiology, recombinant DNA, and immunology. See, for example, Maniatis et al. (1982) Molecular Cloning, A Laboratory Manual, latest edition, Cold Spring Harbor Laboratory, Cold Spring Harbor, N.Y.; Sambrook et al. (1989) Molecular Cloning: A Laboratory Manual, latest edition (Cold Spring Harbor, N.Y.: Cold Spring Harbor Laboratory Press); Ausubel et al. (1992) Current Protocols in Molecular Biology, latest edition (New York: John Wiley & Sons); Guthrie & Fink (1991) Methods Enzymol. 194:1-863; Cell Biology, A Laboratory Manual, ed. Celis, J. E., Academic Press, NY; Histochemistry, Pearse, A. G. E., Vol. 1 (1980), Vol. 2 (1985), and Vol. 3 (1990).

In the following description, reference will be made to various methodologies well-known to those skilled in the art of immunology. Standard reference works setting forth the general principles of immunology include Klein, J., Immunology: The Science of Cell-Noncell Discrimination, John Wiley & Sons, New York (1982); Kennett, R et al., Monoclonal Antibodies, Hybridoma: A New Dimension in Biological Analyses, Plenum Press, New York (1980); Campbell, A, "Monoclonal Antibody Technology," in Laboratory Techniques in Biochemistry and Molecular Biology, Vol. 13, Burdon, R., et al., eds., Elsevier, Amsterdam (1984); and Eisen, H. N., Microbiology, 3rd ed, Davis, B. D., et al., Harper & Row, Philadelphia (1980).

The invention provides methods and compositions for preventing thrombus formation by targeting Sf2 with a Sf2 antagonist. More specifically, the invention provides that Sf2 directly affects thrombus formation via modulation of factor XIa and activation of protein C, and Sf2 deficiency or inactivation can be used prophylactically against the development of venous thromboembolism.

In certain embodiments, the invention for the first time provides that Sf2 directly affects acute and chronic thrombus formation in vivo. Similar to previous reports with prophylactic anticoagulants, the invention demonstrates that Sf2-deficiency or prophylactic administration of Sf2 antibodies markedly reduced venous thrombus formation, indicating that prophylactic therapies that target Sf2 can effectively prevent the formation of thrombosis and its associated complications.

In certain embodiments, the invention provides a method for preventing thrombus formation or complications associated therewith in an individual in need comprising administering to the individual a thrombus prophylactic amount of a composition comprising a Sf2 antagonist and a pharmaceutically acceptable carrier. In certain embodiments, the invention provides a method for preventing thrombus formation or complications associated therewith comprising administering to an individual in need an prophylaxis effective amount of a Sf2 antagonist that reduces Sf2 activity or concentration.

In certain embodiments, the therapeutic agent is a Sf2 antagonist that directly or indirectly interferes with or inhibits Sf2 causing Sf2-deficiency. In certain embodiments, the therapeutic agent is an antibody, a peptide, a nucleic acid, a receptor decoy, a ribozyme, a sense polynucleotide, a double stranded RNA, a RNAi, a DNA aptamer, a chemical agent or other small molecule, naturally occurring or synthetically produced, with an Sf2 antagonist ability, such as the ability to interfere with or inhibit Sf2 causing Sf2 deficiency.

In certain embodiments, the Sf2 antagonist inhibits, suppresses, blocks, or interferes with Sf2 activity level by directly binding to active sites on Sf2, or indirectly by binding other regions of Sf2 to sequester or otherwise reduce or diminish Sf2 activity, and thereby preventing thrombus formation. As used herein, Sf2 antagonist refers to an agent that inhibits, suppresses, blocks, or interferes with Sf2 gene, protein, and/or activity level, causing Sf2-deficiency. The invention encompasses any Sf2 antagonists, now known or later developed. Methods for screening and/or identifying a Sf2 antagonist are well-known in the art and are contemplated by the scope of the invention.

In some embodiments, Sf2 antagonists can be determined under immunoassay conditions. Under designated immunoassay conditions, Sf2 antibodies (or other types of antagonists) bind to Sf2 and do not bind in a significant amount to other polypeptides present in the sample. Selective binding of a molecule, such as an antibody, to Sf2 can include selectivity for a particular epitope or peptide of Sf2. A variety of immunoassay formats may be used to select antibodies that selectively bind with a particular polypeptide of Sf2. For example, solid-phase ELISA immunoassays are routinely used to select antibodies selectively immunoreactive with a polypeptide. See Harlow and Lane, "Antibodies, A Laboratory Manual," latest edition, Cold Spring Harbor Publications, New York, (1988), for a description of immunoassay formats and conditions that can be used to determine selective binding.

In certain embodiments, the therapeutic agent is a Sf2 antibody, or a functional fragment thereof, including but not limited to, a monoclonal or polyclonal antibody, a recombinant or naturally occurring antibody, a human or humanized antibody, and a chimeric antibody. The term "antibody" (Ab) is meant to include intact molecules as well as antibody fragments (such as, for example, $F_v$, $F_{ab}$ and $F_{(ab')2}$ fragments), single chain antigen-binding proteins, "humanized" antibodies, and chimeric antibodies which are capable of specifically binding to Sf2. $F_{ab}$ and $F_{(ab')2}$ fragments lack the $F_c$ fragment of intact antibody, clear more rapidly from the circulation, and may have less non-specific tissue binding of an intact antibody.

The invention encompasses any Sf2 antibody, now known or later developed from any animal species or from humans. Methods for developing and/or producing Sf2 antibody from a mammal or methods for humanizing an antibody are well known in the art and are contemplated by the scope of the invention. Exemplarily Sf2 antibody suitable for use in the invention includes, but is not limited to, Sf2 antibody 4h9 (innov-research.com/product/inhibitory-mouse-monclonal-to-mouse-antiplasmin-map4h9/), Sf2 antibody 27c9 (innov-research.com/product/inhibitoty-mouse-monclonal-mouse-antiplasmin-map27c9/), Innovative Research), and TS23 (Translational Sciences).

U.S. Pat. Nos. 6,114,506, 9,150,903, and U.S. Publication No. 20140220034 to Reed et al. disclose certain other uses for Sf2 antagonists, including but not limited to MAb 49C9, 70B11, 77A3, and RWR (and their fragments), all of which molecules (and the amino acid sequences of the binding regions of the immunologic molecules) are herein incorporated by reference.

Further exemplary Sf2 antagonists include the following commercially available antibodies: monoclonal antibodies to MAP4H9 (Molecular Innovations), 27C9 (Molecular Innovations), 14AP (Fitzgerald Industries), MPW14AP (antibodies-online GmbH), 3617 (American Diagnostics), goat polyclonal antibody to Sf2 (Biopool), and other anti-human polyclonal and monoclonal antibodies to Sf2 available from Genetex, Thermo Scientific Pierce Protein Research Products. The invention also contemplates the use of humanized and human antibodies constructed through molecular biology techniques.

Antibodies suitable for use in the present invention may be prepared by a variety of methods. For example, cells expressing Sf2 (or fractions, lysates, etc. thereof) can be administered to an animal in order to induce the production of sera containing polyclonal antibodies that are capable of binding Sf2. In some methods, a preparation of Sf2 antibody is prepared and purified to render it substantially free of natural contaminants. Such a preparation is then introduced into an animal in order to produce polyclonal antisera of greater specific activity.

Antibodies may also be prepared using phage display technology. Methods of preparing antibodies using phage display are known in the art. See, for example, U.S. Pat. No. 5,565,332; Clarkson et al., 1991, Nature 352:624-628; Huse, 1989, Science 246:1275-1281; Kang, 1993, Proc. Natl. Acad. Sci. USA 88:11120-11123; Marks, 1991, J. Mol. Biol. 222:581-597; and McCafferty et al., 1990, Nature 348:552-554.

In some instances, it is desirable to prepare monoclonal antibodies from various hosts. A description of techniques for preparing such monoclonal antibodies may be found in Stites et al. eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988. For example, monoclonal antibodies can be prepared using hybridoma technology. In general, such procedures involve immunizing an animal (frequently a mouse) with the antigen or with a cell which expresses the antigen. A preferred antigen is purified Sf2 or a fragment thereof. Suitable cells can be recognized by their capacity to secrete anti-Sf2 antibody. Such cells may be cultured in any suitable tissue culture medium, for example, in Earle's modified Eagle's medium supplemented with 10% fetal bovine serum (inactivated at about 56° C.), and supplemented with about 10 ug/l of nonessential amino acids, about 1,000 U/ml of penicillin, and about 100 ug/ml of streptomycin. The splenocytes of such mice are extracted and fused with a suitable myeloma cell line. The method of somatic cell fusion is described in Galfre, G. and Milstein, C., Meth. Enzymol. 73:3-46 (1981). After fusion, the resulting hybridoma cells are selectively maintained in HAT medium, and then cloned by limiting dilution as described by Wands et al., 1981, Gastroenterology 80:225-232. The hybridoma cells obtained through such a selection are then assayed to identify clones which secrete antibodies capable of binding Sf2.

It will be appreciated that $F_{ab}$ and $F_{(ab')2}$ and other fragments of the antibodies of the present invention may be used according to the methods disclosed herein. Such fragments are typically produced by proteolytic cleavage, using enzymes such as papain (to produce $F_{ab}$ fragments) or pepsin (to produce $F_{(ab')2}$ fragments). Alternatively, Sf2 antagonist fragments can be produced through the application of recombinant DNA technology, through synthetic chemistry, biotinylation, or any other suitable means known in the art.

Also within the scope of the present invention are humanized or chimeric antibodies, produced using genetic constructs derived from hybridoma cells producing MAbs. Humanized antibodies are antibodies in which the framework or other regions of the murine Ab is replaced with the homologous regions of a nonmurine antibody. Chimeric antibodies are antibodies in which the murine constant region has been replaced with a non-murine constant region. Methods for production of chimeric antibodies are known in the art. See, for review: Morrison, Science, 229:1202-1207 (1985); Oi et al., BioTechniques 4:214 (1986); see also, Cabilly et al., U.S. Pat. No. 4,816,567 (Mar. 28, 1989); Taniguchi et al., EP171496 (Feb. 19, 1986); Morrison et al., EP173494 (Mar. 5, 1986); Neuberger et al., WO8601533 (Mar. 13, 1986); Robinson et al., WO 8702671 (May 7, 1987); Boulianne et al., Nature 312:643-646 (1984); and Neuberger et al., Nature 314:268-270 (1985). Methods for production of humanized antibodies are known in the art. See, for example, U.S. Pat. No. 5,585,089; Jones et al., Nature 321:522-525 (1986); and Kettleborough et al., Protein Engineering 4:773-783 (1991).

Also provided in the present invention are antibodies capable of binding to both (1) human and nonhuman circulating Sf2 and (2) human and nonhuman fibrin crosslinked Sf2. Such antibodies are well known in the art. See, for example, U.S. Pat. Nos. 4,946,778; 5,260,203; 5,091,513; and 5,455,030, all of which are herein incorporated by reference. Also within the scope of the present invention are variants of the antibodies described above.

In some embodiments, MAbs are generated by somatic cell fusion, selected for specific binding to Sf2, cloned and purified as described (Reed, G. L. Functional characterization of monoclonal antibody inhibitors of alpha 2-antiplasmin that accelerate fibrinolysis in different animal plasmas. Hybridoma 1997; 16: 281-286). The serotypes of these MAbs are: 49 ($I_{g\gamma 2a}K$), 77 ($I_{g\gamma 2a}K$), RWR ($I_{g\gamma 1a}K$). In some embodiments, polyclonal antibodies are generated against peptides that mimic the NH2-terminus and COOH-terminus as described in Reed et al. 1992, Thromb Haemost 68:315-320.

Also provided in the present invention are Sf2 antagonists which are specifically not antibodies or fragments thereof. Screening for such Sf2 antagonists is routine in the art. Particular known compounds of interest or libraries of compounds generated through combinatorial chemistry techniques, for example, can be screened for the desired binding and conversion activity. Furthermore, phage display technology can be used to identify peptides, for example, for the desired binding and conversion activity. In general, phage display describes a selection technique in which a library of variants of a peptide or protein is expressed on the outside of a phage virion, while the genetic material encoding each variant resides on the inside (Sidhu et al., 2003, Chembiochem. 4:14; Ferrer et al., 1999, J. Pept. Res.: 54, 32; BouHamdan et al., 1998, J. Biol. Chem. 273: 8009). This creates a physical linkage between each variant protein sequence and the DNA encoding it, which allows rapid partitioning based on binding affinity to a given target molecule by an in vitro selection process called panning (Whaley et al., 2000, Nature, 405, 665). In its simplest form, panning is carried out by incubating a library of phage-displayed peptides with a plate (or bead) coated with the target, washing away the unbound phage, and eluting the specifically bound phage. The eluted phage is then amplified and taken through additional binding/amplification cycles to enrich the pool in favor of binding sequences. After 3-4 rounds, individual clones are characterized by DNA sequencing and ELISA. Many variations of the phage display technology are known to those of skill in the art which can be adapted for purposes of the present invention.

In one embodiment, a phage display peptide library is used such as provided by New England Biolabs (Mass, Mass.). The pre-made random peptide libraries, Ph.D. libraries, have been used for myriad similar applications, including epitope mapping, identification of protein-protein contacts (Rozinov and Nolan, 1998, Chem. Biol. 5:713-28) and enzyme inhibitors (Rodi et al., 1999, J. Mol. Biol. 285:197-203).

As used herein, the term "patient" or "individual" is a human or nonhuman mammal. As used herein the term "administering" refers to various means of introducing a composition into a cell or into a patient. These means are well known in the art and may include, for example, injection or infusion for parenteral delivery; tablets, pills, capsules, or other solids for oral administration; nasal solutions or sprays; aerosols; inhalants; topical formulations; liposomal forms; and the like. As used herein, the terms "prophylactic amount", "effective amount" and "therapeutic amount" refer to an amount that will provide the desired result and may readily be determined by one of ordinary skill in the art depending upon the specific activity of the chosen Sf2 antagonist and the condition of the patient.

In some embodiments, pharmaceutical compositions are provided that comprise an effective amount of a Sf2 antagonist. These pharmaceutical compositions are useful for preventing thrombus formation or complications associated therewith.

Suitable pharmaceutical compositions in accordance with the invention can generally include an amount of the active ingredient admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and purity standards as required.

The compositions of the present invention may be formulated for various means of administration. As used herein, the term "route" of administration is intended to include, but is not limited to subcutaneous injection, intravenous injection, intraocular injection, intradermal injection, intramuscular injection, intraperitoneal injection, intratracheal administration, epidural administration, inhalation, intranasal administration, oral administration, sublingual administration, buccal administration, rectal administration, vaginal administration, and topical administration. The preparation of an aqueous composition that contains a peptide, antibody or antibody fragment, antisense nucleic acid, receptor decoy, ribozyme, sense polynucleotide, double stranded RNA, RNAi, aptamer, or small molecule agonist, as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The compositions of the present invention can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, preparations generally should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate, and gelatin.

Prior to or upon formulation, the compositions of the present invention may be dialyzed to remove undesired small molecular weight molecules, and/or lyophilized for more ready formulation into a desired vehicle, where appropriate. Sterile injectable solutions can be prepared by incorporating the active agents in the required amount in the appropriate solvent with various of the other ingredients enumerated above, as desired, followed by filter sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

In some embodiments, the methods comprise co-administering to the patient a Sf2 antagonist and an additional agent that operates to, directly or indirectly, help prevent thrombus formation. Such additional agent may be administered separately or co-administered with the disclosed Sf2 antagonist. The term "co-administration" is intended to mean that the Sf2 antagonist and additional agent will be administered during a time frame wherein the respective periods of pharmacological activity overlap. The Sf2 antagonist and additional agent may be administered simultaneously or sequentially. In some embodiments, the Sf2 antagonist can be co-administered an effective amount of a pharmaceutically active agent selected from the group consisting of an anticoagulant, a plasminogen activator, an antiplatelet and a pro-fibrinolytic agent.

In some embodiments, pharmaceutical methods may be employed to control the duration of action. Controlled release preparations may be achieved by the use of polymers to complex or absorb Sf2 antagonists. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate). The rate of Sf2 antagonist release may also be controlled by altering the concentration of such macromolecules. Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system, for example, liposomes, albumin microspheres, microemulsions, nanoparticles, nanocapsules, or in macroemulsions. Such teachings are disclosed in Remington's Pharmaceutical Sciences, 16th Ed., Osol, A., ed., Mack, Easton Pa. (1980).

In certain embodiments, the invention method is used for preventing thrombus formation or complications associated therewith due to surgery, immobility, genetic abnormality, cancer, trauma, or other risk factor.

In certain embodiments, the invention provides a composition for preventing thrombus formation or complications associated therewith in a patient at risk comprising a prophylactic amount of a therapeutic agent targeting Sf2.

In certain embodiments, the invention composition further comprises a physiologically acceptable carrier, solvent, or excipient. The invention contemplates any such carriers, solvents, or excipients now known or later developed in the art.

Other embodiments and uses are apparent to one skilled in the art in light of the present disclosures. Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

Throughout the specification various publications and citations are referenced, and the entire content of each is hereby incorporated by reference. The following example is provided to describe the invention in more detail. It is intended to illustrate, not to limit the invention.

EXAMPLES

Example 1

Material & Methods

Methods

Animal studies were approved by the Institutional Animal Use and Care Committee. C57Bl6 mice with normal Sf2 levels ($Sf2^{+/+}$) or Sf2-deficiency ($Sf2^{-/-}$) were studied.

Venous Thrombosis

Mice were anesthetized with 2 percent isoflurane and maintained at 1-2 percent with a nose cone. They were placed in a dorsal recumbent position on a heating pad at 37 deg. The anterior abdomen was shaved. The abdomen was sprayed with chlorhexidine solution and wiped with sterile gauze until the surgical site was clean. A midline incision was made to open the abdomen. Following visualization of the inferior vena cava (IVC), the isoflurane was reduced to a maintenance level of 1-2% and the oxygen rate remains at 0.2 liters per minute consistent with adequate anesthesia.

In some experimental groups human Sf2 (4.9 mg/kg, Athens Research), or Sf2 antibodies (10 mg/kg, 4h9 (innov-research.com/product/inhibitory-mouse-monclonal-to-mouse-antiplasmin-map4h9/), Sf2 antibody 27c9 (innov-research.com/product/inhibitory-mouse-monclonal-to-mouse-antiplasmin-map4h9/), innovative Research) or TS23 (Translational Sciences) were administered via a side branch of the IVC. Then all WC side branches, from the renal veins to the iliac bifurcation, are ligated with 7-0 non-reactive prolene sutures. The WC, was ligated below the renal arteries and thrombus subsequently developed. The laparotomy site was dosed in a two-layer fashion. Buprenorphine 0,05-0.1 mg/kg SQ was given as a post-operative analgesic for mice. At the assigned time point, euthanasia was performed humanely using approved methods. Blood was isolated by cardiac puncture. The IVC was carefully stripped of adherent tissue from just above the ligation to the iliac bifurcation and weighed. The thrombus weight was determined by subtracting the average weight of the vena cava in sham mice subjected to the same surgery without vena caval ligation, from the weight or vena cava and thrombus in mice undergoing vena caval ligation. Thrombus weight was normalized to mouse weight.

Statistics

Data were analyzed by a one way ANOVA using the Neuman-Keuls correction. A p-value <0.05 was considered significant.

Example 2

Sf2-Deficiency Prevents Thrombus Formation

Figure 1B:
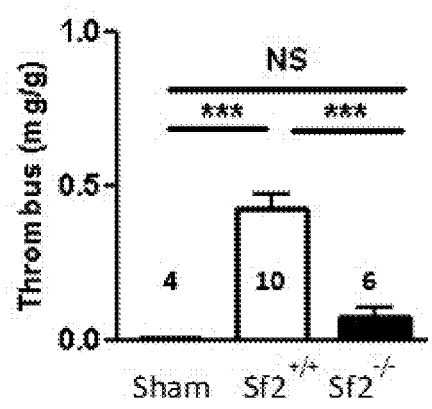

Previous studies have shown that venous clots or thrombi develop over the course of hours reaching a maximum approximately 24 h after vena cava ligation.[8] To determine whether Sf2 affects early thrombus development, mice were examined 5 hrs. after ligation of the vena cava. In sham mice that underwent the surgical procedure without ligation of the vena cava, there was no detectable thrombus formation (FIGS. 1A and 1B). Control ($Sf2^{+/+}$) mice developed large thrombi that occluded the vena cava all the way to the iliac veins. By comparison, thrombus formation was largely eliminated in congenic Sf2-deficient ($Sf2^{-/-}$) mice. Examination of the cross-section of a typical venous thrombus from Sf2+/+ mice showed venous obstruction with a fibrin-rich thrombus as detected by Martius scarlet blue staining; there was no significant thrombus seen in $Sf2^{-/-}$ mice. When the vein weight is considered, the thrombus weights in $Sf2^{+/+}$ mice were >3-fold greater than detected in $Sf2^{-/-}$ mice (FIG. 1, p<0.001). Taken together, these data indicate that Sf2-deficiency prevents thrombus formation.

Example 3

Sf2 Antibody Inhibits Thrombus Formation Directly Regulated by Sf2

Figure 2:
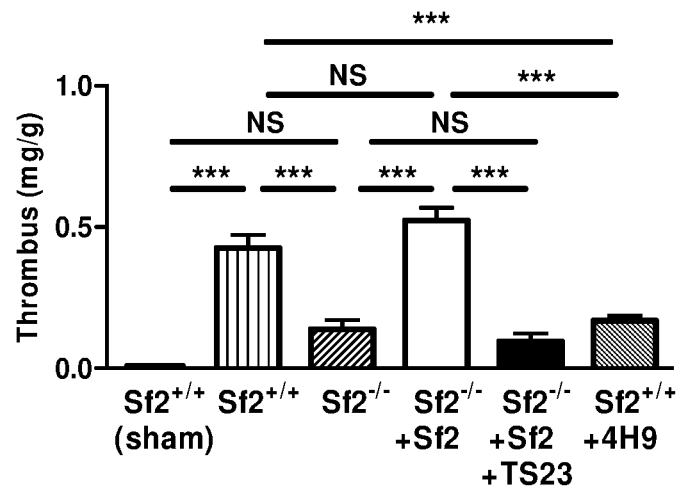
FIG. 2 shows that Sf2 activity is required for early thrombus formation. Early venous thrombosis was examined in various experimental groups. Sham mice (no venous ligation), control mice ($Sf2^{+/+}$), Sf2-deficient ($Sf2^{-/-}$) mice, Sf2-deficient mice given physiologic amounts of human Sf2 ($Sf2^{-/-}$+Sf2), Sf2-deficient mice given human Sf2 and a human Sf2 inactivating antibody (Sf2$^{-/-}$+Sf2+TS23) and normal mice given an antibody that inactivates mouse Sf2 (Sf2$^{+/+}$+4H9). Mean±SEM thrombus weights normalized to mouse body weight (mg/g). Numbers of mice per group are shown. Control (Sf2$^{+/+}$, N=7F, 4M), sham (N=4M), Sf2$^{-/-}$ (N=11F), Sf2$^{-/-}$+Sf2 (N=7F), Sf2$^{-/-}$+Sf2+TS23 (N=5F, 2M), Sf2$^{+/+}$+4H9 (N=7, 4F, 3M). Mean±SEM, ***$p<0.001$, ANOVA, Newman-Keuls correction.

Gene deletion can produce compensatory changes in animals that may affect outcomes. To confirm that Sf2 was directly responsible for thrombus formation, physiologic levels of Sf2 were administered to mice prior to vein ligation. When compared to control, Sf2$^{+/+}$ mice, Sf2$^{-/-}$ mice given Sf2 had similar size venous thrombus formation (FIG. 2). In contrast, Sf2$^{-/-}$ mice given physiologic amounts of human Sf2 had >3-fold larger thrombi than Sf2$^{-/-}$ mice (p<0.001).

To provide additional evidence that Sf2 was responsible for early thrombus formation, an anti-human Sf2 antibody (TS23) was administered to Sf2$^{-/-}$ mice that were given Sf2. The Sf2 antibody markedly reduced thrombus formation in Sf2$^{-/-}$ mice given Sf2; indeed the reduction in thrombus size was comparable to the levels seen in Sf2$^{-/-}$ mice not receiving Sf2. In a similar fashion, another anti-mouse Sf2 antibody (4H9) prevented thrombus formation in Sf2$^{+/+}$ mice by comparison to Sf2$^{+/+}$ mice receiving no Sf2 antibody (p<0.001). Inhibition of thrombus formation was also seen in mice treated with another anti-mouse Sf2 antibody, 27C9 (not shown). Taken together, these data indicate that Sf2 itself regulates thrombus formation and that prophylactic administration of a Sf2 antibody can inhibit thrombus formation.

Figure 3:
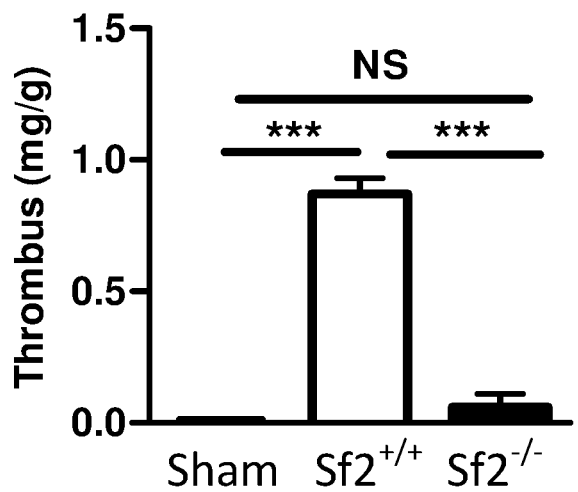
FIG. 3 shows that Sf2 has prolonged effects on thrombus formation. Thrombus formation was assessed 7 days after ligation of the vena cava in sham, control (Sf2$^{+/+}$) and Sf2-deficient (Sf2$^{-/-}$) mice. Mean±SEM thrombus weights normalized to mouse body weight (mg/g). Sham (N=5M), Sf2$^{+/+}$ (N=7F, 43M), Sf2$^{-/-}$ (N=5M, 4F) ***$p<0.001$, NS, not significant.

Since thrombus formation proceeds over the course of many hours, it was determined whether the early reductions in venous thrombus seen Sf2-deficient mice were persistent. By comparison to sham mice, in control Sf2$^{+/+}$ mice there was significant thrombus formation seen at 7 days post ligation of the vena cava (FIG. 3, p<0.001). In fact, in control mice, the thrombi at 7 days were more than twice as large as those seen at 5 hrs. (FIG. 2 vs. FIG. 3). In contrast, 7 days post ligation of the vena cava, there was no significant thrombus formation seen in Sf2-deficient mice by comparison to sham mice, or by comparison to Sf2-deficient mice at 5 hrs. (p, NS).

REFERENCES

1. Huang W, Goldberg R J, Anderson F A, Kiefe C I, Spencer F A. Secular trends in occurrence of acute venous thromboembolism: The worcester vte study (1985-2009). *The American Journal of Medicine*. 2014; 127:829-839 e825
2. Shorr A F. The pharmacoeconomics of deep vein thrombosis treatment. *Am J Med*. 2007; 120:S35-41
3. Beckman M G, Hooper W C, Critchley S E, Ortel T L. Venous thromboembolism: A public health concern. *American Journal of Preventive Medicine*. 38:S495-501
4. Guyatt G H, Akl E A, Crowther M, Gutterman D D, Schuunemann H J. Executive summary: Antithrombotic therapy and prevention of thrombosis, 9th ed: American college of chest physicians evidence-based clinical practice guidelines. *Chest*. 2012; 141:7S-47S
5. Hirsh J, O'Donnell M, Weitz J I. New anticoagulants. *Blood*. 2005; 105:453-463
6. Saito H, Goldsmith G H, Moroi M, Aoki N. Inhibitory spectrum of alpha 2-plasmin inhibitor. *Proc Natl Acad Sci USA*. 1979; 76:2013-2017
7. Heeb M J, Gruber A, Griffin J H. Identification of divalent metal ion-dependent inhibition of activated protein c by alpha 2-macroglobulin and alpha 2-antiplasmin in blood and comparisons to inhibition of factor xa, thrombin, and plasmin *J Biol Chem*. 1991; 266:17606-17612
8. Aghourian M N, Lemarie C A, Blostein M D. In vivo monitoring of venous thrombosis in mice. *J Thromb Haemost*. 2012; 10:447-452

What is claimed is:

1. A method for inhibiting thrombosis in a human individual in need comprising administering to the individual a thrombosis prophylactic amount of a composition comprising an anti-Serpin f2 (Sf2) antibody, or a functional fragment thereof, that inhibits Sf2-dependent thrombosis, and a pharmaceutically acceptable carrier, wherein prior to the administering step the subject has not been determined to have a thrombus.

2. The method of claim 1, wherein the Sf2 antibody or functional fragment thereof is monoclonal.

3. The method of claim 1, wherein the Sf2 antibody or functional fragment thereof is recombinant or naturally occurring.

4. The method of claim 1, wherein the Sf2 antibody or functional fragment thereof is chimeric, human or humanized.

5. The method of claim 1, wherein the antibody is MAb 49 or MAb 77 or a functional fragment thereof.

6. The method of claim 1, wherein the antibody is TS23 or a functional fragment thereof.

7. The method of claim 1, wherein the subject is at risk for thrombus formation due to immobility, genetic abnormality, cancer, or other risk factor.

8. The method claim 1, further comprising co-administering with the composition an effective amount of a pharmaceutically active agent selected from the group consisting of an anticoagulant, an antiplatelet and a pro-fibrinolytic agent.

9. The method of claim 1, wherein the administration step does not include a plasminogen activator.

10. The method of claim 1, further comprising an earlier step of selecting the anti-Serpin f2 (Sf2) antibody, or a functional fragment thereof, for an ability to inhibit Sf2-dependent thrombosis.

* * * * *